United States Patent
Malkar et al.

(10) Patent No.: US 7,790,921 B2
(45) Date of Patent: Sep. 7, 2010

(54) METHODS FOR THE PREPARATION, FORMULATION AND USE OF LITHIUM VALPROATE

(75) Inventors: Navdeep B. Malkar, Cary, NC (US); Deanna Jean Nelson, Raleigh, NC (US); Walter C. Holberg, III, Apex, NC (US)

(73) Assignee: Biolink Life Sciences, Inc., Cary, NC (US)

( * ) Notice: Subject to any disclaimer, the term of this patent is extended or adjusted under 35 U.S.C. 154(b) by 0 days.

(21) Appl. No.: 12/082,878

(22) Filed: Apr. 15, 2008

(65) Prior Publication Data

US 2008/0234514 A1 Sep. 25, 2008

Related U.S. Application Data

(63) Continuation of application No. 11/725,414, filed on Mar. 19, 2007, now Pat. No. 7,449,598.

(51) Int. Cl.
*C07B 53/00* (2006.01)

(52) U.S. Cl. .................................................... 562/606
(58) Field of Classification Search ...................... None
See application file for complete search history.

(56) References Cited

OTHER PUBLICATIONS

Abstract, Kharlamov et al., Farmakologiya i Toksikologiya (Moscow) (1984), 47(5), 11-15; CAS online abstract [retrieved Dec. 8, 2008] from STN, Columbus, OH, USA.*

Abstract, Glinka et al., Zeszyty Naukowe—Politechnika Lodzka, Technologia i Chemia Spozywcza (1995), 718(54), 83-92 ; CAS online abstract [retrieved Dec. 8, 2008] from STN, Columbus, OH, USA.*

* cited by examiner

*Primary Examiner*—Karl J Puttlitz
(74) *Attorney, Agent, or Firm*—Casimir Jones, S.C.

(57) ABSTRACT

The present invention relates to methods for preparing lithium valproate and administering this compound to a subject in need of treatment with lithium and/or valproate. Pharmaceutical compositions are also provided that are useful therapies for the treatment of neurological, immunological, and viral-mediated disorders in warm-blooded mammals.

4 Claims, 2 Drawing Sheets

METHODS FOR THE PREPARATION, FORMULATION AND USE OF LITHIUM VALPROATE

CROSS-REFERENCE TO RELATED APPLICATION

This is a continuation of application Ser. No. 11/725,414 filed Mar. 19, 2007 now U.S. Pat. No. 7,449,598, of the same title.

FIELD OF THE INVENTION

The present invention relates to methods for preparing lithium valproate, its pharmaceutical formulations, and administering this compound to a subject in need of treatment with lithium and/or valproate. Pharmaceutical compositions are also provided that are useful therapies for the treatment of neurological, immunological, and retroviral-mediated disorders in warm-blooded mammals.

BACKGROUND OF THE INVENTION

The National Institute of Neurological Disorders and Stroke sponsored a recent survey of twelve neurological disorders which confirms that the burden of neurologic illness affects many millions of people in the United States. [Hirtz D, Thurman D J, Gwinn-Hardy K, Mohamed M, Chaudhuri A R, Zalutsky R. How common are the "common" neurologic disorders? Neurology 2007 Jan. 30; 68(5): 326-37.] The data indicate that more than two million people in the U.S. (i.e., slightly more than seven per 1,000) have epilepsy. Similarly, more than 35 million individuals live with migraines, a prevalence of 121 out of 1,000.

Likewise, bipolar disorder (BPD) is a prevalent and debilitating manic-depressive illness, affecting approximately 1% of the population worldwide. BPD, a psychosis characterized by cyclic periods of mania and depression, is associated with significant morbidity and mortality, with suicide as a cause of death in as many as 10% of patients. Little is known about the pathogenesis of BPD, but it responds remarkably well to mood-stabilizing drugs, such as lithium ion (lithium), and the anticonvulsant valproate.

Further, as many as 900,000 Americans are infected with the human immunodeficiency virus (HIV). Before the arrival of modern antiviral therapies in the late 1990's, HIV effected rapidly devastating effects on the brain known as HIV-associated dementia (HAD) or neuroAIDS. The current, standard combination of HIV treatments (also known as highly active antiretroviral treatment or HAART) has extended the lives of most U.S. AIDS patients, but has not cured neuroAIDS, despite early reports to the contrary. Current antiviral combinations slow the onset of HIV-related nerve damage that becomes more common the longer HIV patients live. Therefore, whereas patients suffered rapid, severe neurological damage before HAART therapy, they now gradually lose attention span, memory, speaking ability and decision-making skills despite the best available treatment.

Clinical Uses

Valproic acid (valproate) has been approved by regulatory agencies around the world, including the U.S. Food and Drug Administration (FDA), as a therapy for several clinical indications, including neurological disorders, mania, manic episodes associated with bipolar disorder, epilepsy, and affective and attention deficit disorders. In addition, valproate is used for the prophylactic treatment, modulation and management of migraine headache, chronic pain, and neuropathic pain.

Although the underlying therapeutic mechanisms are unclear, a growing body of evidence suggests that valproate has neuroprotective and neurotrophic actions. For example, both brain imaging and post-mortem studies demonstrate that bipolar disorder involves a decrease in the volume and number of neurons and glia in discrete brain areas thought to be important for cognition and mood regulation. Remarkably, the reduction in brain volume in bipolar patients was found to be largely suppressed by chronic treatment with valproate, in part as a consequence of its histone deacetylase inhibition. [Kanai H, Saws A, Chen R W, Leeds P, Chuang D M. Valproic acid inhibits histone deacetylase activity and suppresses excitotoxicity-induced GAPDH nuclear accumulation and apoptotic death in neurons. Pharmacogenom J 2004; 4: 336-344.] Likewise, in cellular models, valproate protects rat cerebral cortical neurons and cerebellar granule cells from glutamate-induced excitotoxicity and apoptotic death from stress on the endoplasmic reticulum in C6 glioma cells and PC12 cells. [Bown C D, Wang J F, Chen B, Young L T. Regulation of ER stress proteins by valproate: therapeutic implications. Bipolar Disord 2002; 4: 145-151.] In a rat model of stroke, post-insult valproate treatment reduces ischemia-induced brain damage, caspase-3 activation and neurological deficits. [Ren M, Leng Y, Jeong M, Leeds P R, Chuang D M. Valproic acid reduces brain damage induced by transient focal cerebral ischemia in rats: potential roles of histone deacetylase inhibition and heat shock protein induction. J Neurochem 2004; 89: 1358-1367.] A number of studies report that valproate activates cell survival factors such as Akt, extracellular signal-regulated protein kinase, and cyclic AMP response element binding protein. [De Sarno P, Li X, Jope R S. Regulation of Akt and glycogen synthase kinase-3 beta phosphorylation by sodium valproate and lithium. Neuropharmacology 2002; 43: 1158-1164. Yuan P X, Huang L D, Jiang Y M, Gutkind J S, Manji H K, Chen G. The mood stabilizer valproic acid activates mitogen-activated protein kinases and promotes neurite growth. J Biol Chem 2001; 276: 31674-31683. Einat H, Yuan P, Gould T D, Li J, Du J, Zhang L, et al. The role of the extracellular signal-regulated kinase signaling pathway in mood modulation. J Neurosci 2003; 23: 7311-7316.] Additionally, valproate induces cytoprotective proteins such as Bcl-2, Grp78, brain-derived neurotrophic factor, and heat-shock protein 70. [Chen G, Zeng W Z, Yuan P X, Huang L D, Jiang Y M, Zhao Z H et al. The mood-stabilizing agents lithium and valproate robustly increase the levels of the neuroprotective protein bcl-2 in the CNS. J Neurochem 1999; 72: 879-882.] Moreover, valproate promotes neurite outgrowth. [Yuan P X, Huang L D, Jiang Y M, Gutkind J S, Manji H K, Chen G. The mood stabilizer valproic acid activates mitogen-activated protein kinases and promotes neurite growth. J Biol Chem 2001; 276: 31674-31683.] Recently, valproate was shown to protect dopaminergic neurons in midbrain neuron/glia cultures by stimulating the release of neurotrophic factors from astrocytes. [Chen P-S, Peng G-S, Li G, Yang S, Wu X, Wang C-C, Wilson B, Lu R-B, Gean P-W, Chuang D-M, Hong J-S. Valproate protects dopaminergic neurons in midbrain neuron/glia cultures by stimulating the release of neurotrophic factors from astrocytes. Molec Psych 2006; 11: 1116-1125.] Further, valproate at therapeutic levels was reported to inhibit histone deacetylase (HDAC), an enzyme that catalyzes the remove of acetyl groups from lysine residues of histones, thereby altering gene expression. [Phiel C J, Zhang F, Huang E Y, Guenther M G, Lazar M A, Klein P S. Histone deacetylase is a direct target of valproic acid, a potent anticonvulsant, mood stabilizer, and teratogen. J Biol Chem 2001; 276:

36734-36741. Gottlicher M, Minucci S, Zhu P, Kramer O H, Schimpf A, Giavara S et al. Valproic acid defines a novel class of HDAC inhibitors inducing differentiation of transformed cells. EMBO J 2001; 20: 6969-6978.]

Further, potential therapeutic benefits of valproate in still other clinical indications are being evaluated in on-going clinical trials. Valproate therapy is being evaluated in clinical studies assessing activity of the substance as a histone deacetylase inhibitor to promote cell differentiation and regeneration, or to regulate gene expression in subjects afflicted with spinal muscular atrophy. Likewise, valproate may exhibit therapeutic benefit as a combinatorial therapeutic treatment of human cancers and for the treatment of tumor metastasis. Similarly, valproate may be useful in the treatment and management of pain, for treating severe tinnitus, for treatment of disorders of personal attachment and deficient social interaction, or for treating Alzheimer's disease. Preclinical studies also show that valproate may promote neural stem cell differentiation and or be useful as a co-medicament to promote the elimination of the Human Immunodeficiency Virus (HIV) or other retroviruses from the body or to prevent progression of a retroviral infection to AIDS. Clinical investigators have found that both lithium and valproate Lithium is indicated for the treatment of bipolar disorder, both for treatment of acute mania and for prophylaxis against recurrence. Other psychiatric conditions that may be benefited by administration of lithium include recurrent severe depressions without manic episodes, schizoaffective psychosis, episodic alcoholism, periodic antisocial behavior, and periodic schizophrenic illness.

Sources of the Active Pharmaceutical Ingredient Valproate

Valproic acid (Chemical Abstracts Service (CAS) Registry No. 99-66-1) is a branched carboxylic acid having the molecular formula $C_8H_{16}O_2$. Valproic acid is also known as 2-propylpentanoic acid, 2-propylvaleric acid, and dipropylacetic acid. Valproic acid is a colorless liquid having a boiling point of 120-121° C. at 14 torr. The compound is very slightly soluble in water. It has a pKa of 4.6, and reacts with bases to form salts generally known as valproates.

Although valproate is a therapeutically active pharmaceutical ingredient, valproic acid is an oil that is difficult to formulate and use in the preparation of dosage forms suitable for human or veterinary use. In addition, the administration of valproic acid to subjects requiring its therapeutic administration results in the exhibition of deleterious side effects, including gastrointestinal distress and ulceration. Pharmaceutical and pharmacological advantages are gained when therapeutic dosage forms are prepared from alkali metal or alkaline earth metal salts of valproic acid. Therefore, alkali metal or alkaline earth metal salts of valproic acid are used in present-day clinical formulations as sources of the active drug ingredient, valproate.

Sodium ($Na^{1+}$), calcium ($Ca^{2+}$) and magnesium ($Mg^{2+}$) valproates have been evaluated for use in pharmaceutical and veterinary compositions. Sodium valproate is a hygroscopic salt that is difficult to formulate into pharmaceutical formulations. In contrast, non-stoichiometric valproate sodium compounds comprising combinations of sodium valproate and valproic acid (divalproex sodium, for example) are not hygroscopic, and are bioavailable and therapeutically active sources of valproate. (The non-stoichiometric compound known as divalproex sodium is disclosed in U.S. Pat. No. 4,988,731, for example, and one of its therapeutic embodiments is described in the FDA Approved Labeling Text for NDA 21-168, Aug. 4, 2000.) At the present time, divalproex sodium is the most commonly formulated source of the drug valproate.

Calcium valproate has also been evaluated for use in pharmaceutical and veterinary formulations. Methods for the preparation of calcium salts of valproic acid are disclosed in U.S. Pat. No. 4,895,873. Although pharmaceutical formulations comprising calcium valproate have been approved by the regulatory bodies of several countries, the use of this valproate salt has been severely restricted following publication of reports of adverse toxicological and reproductive effects in dogs, rats, mice, rabbits, and rats. (For example, adverse effects caused by calcium valproate administration are reported in "Calcium valproate-induced uterine adenocarcinomas in Wistar rats" by Watkins, Gough, et al. in Toxicology, Vol. 41, pages 35-47, 1993.)

Magnesium valproate is also used in clinical formulations. Magnesium valproate, which has the CAS Registry No. 62859-43-7, a molecular formula of $C_{16}H_{30}O_4Mg$, and a molecular weight of 310.71, is also known as magnesium 2-propylvalerate and as 2-propylpentanoic acid magnesium salt. By weight, its composition is 61.8% carbon, 9.7% hydrogen, 7.8% magnesium, and 20.6% oxygen.

Clinical investigators have reported that magnesium valproate possesses pharmacokinetic properties comparable to sodium valproate or valproic acid, is hydrolyzed to valproic acid and magnesium ions upon absorption in the bloodstream, and has important advantages in comparison with either sodium valproate or valproic acid. Among the therapeutic advantages of magnesium valproate are the clinical observations that magnesium valproate exhibits a slower and more regular absorption rate, which prevents the variations in plasma levels of valproate typically observed when sodium salts of valproic acid are administered. Additional therapeutic benefits are afforded by magnesium ions, which possess anticonvulsant and sedative properties. [X. Rabasseda, Drugs of Today, Vol. 31, No. 3, 1995, pp. 185-190.] In contrast to calcium valproate, which exacerbates malignancy, magnesium valproate is a useful therapy when administered to patients with cervical cancer. For example, Chavez-Blanco et al. have reported that magnesium valproate at a dose between 20 and 40 mg/kg inhibits deacetylase activity and hyperacetylates histones in tumor tissues. [A. Chavez-Blanco, B. Segura-Pacheco, et al., Molecular Cancer Jul. 7, 2005, Vol. 4, pp. 22ff.]

Sources of the Drug Lithium

Lithium is most frequently administered therapeutically for the treatment of neurological dysfunction as lithium carbonate, a white, low-melting powder that is slightly soluble in water and alcohol. Lithium carbonate has a Chemical Abstracts Registry No. of 554-13-3, a molecular formula of $Li_2CO_3$, and a molecular weight of 73.89.

There is no commercial source of lithium valproate. No Chemical Abstracts Registry Number has been assigned to lithium valproate. Its physico-chemical properties have not been reported.

Polytherapy with Lithium and Valproate

Recently there has been a great deal of interest in the use of combinations of therapeutic agents, i.e., "polytherapies," in the treatment of neurological disorders. In routine practice for acute mania, both lithium and valproate, administered as separate entities, are useful as adjuncts to antipsychotic drugs, rather than as monotherapy. The antipsychotic activity of valproate is exhibited relatively quickly after therapeutic doses are administered. In contrast, lithium has a delayed effect, taking a few days to begin, and 2-8 weeks or longer to approach its full effect on mania.

Lambert and other French investigators have reported beneficial therapeutic responses to the concomitant administration of valproate (administered as valpromide) and lithium for the treatment of patients with major affective disorders and schizophrenia. [P. A. Lambert. Acute and prophylactic therapies of patients with affective disorders using dipropylacetamide or valpromide. Proceedings of the 7$^{th}$ World Congress of Psychiatry, Vienna, Jul. 11-16, 1983. G. W. Semadeni. Etude clinique de l'effet normothymique du di-propylacetamide. Acta Psychiatr Belg 1976; 76: 458-466.] That response permitted a reduction in the dosage levels of the psychotropic agent required to maintain optimal improvement, which in turn reduced the overall risk of adverse experiences. Further, long-term administration of combinations of valproate and lithium suggested that these two agents may exert a synergistic effect in bipolar patients that is particularly useful in patients whose symptoms are inadequately controlled by lithium alone. Moreover, the adverse effects observed with the concomitantly administered combination were typically only those noted with the use of either individual agent. No unique adverse effects occurring as a result of the drug combination were reported.

Hayes has completed a retrospective study of clinical cases in which valproate [as Depakote® (sodium hydrogen divalproate; Abbott Laboratories, Inc., McGaw Park, Ill.] or combinations of valproate and lithium were administered to 35 patients, all with major depressive illness, bipolar disorder, or schizoaffective disorder, were retrospectively identified as having received valproate either alone or in combination with lithium, after having failed to respond adequately to previous lithium and/or carbamazepine treatment. [S. G. Hayes, M. D. Long-term valproate use in psychiatric disorders. J. Clin Psychiatry 50 (3, Suppl), pages 35-39.] Clinical evaluation and Global Assessment Scale (GAS) scores indicated that at baseline all but 3 of the patients experienced serious psychiatric symptoms, serious impairment in social or professional functioning, or significant impairment in reality testing. Mean GAS scores after a mean duration of at least 1 year of valproate administration improved in 7 of 9 depressed patients, 12 of 12 patients with bipolar disorder, and 11 of 14 patients with schizoaffective states. For patients with either depressive disorders or mixed bipolar disorders, that mean change represented a level of improvement sufficient to elevate the majority of the patients into the mild symptom range or the virtually asymptomatic state. Patients with bipolar and schizoaffective disorders to valproate treatment compared to valproate plus lithium were evaluated for an average of 11 to 14 months of treatment. Patients in both treatment groups demonstrated very similar and quite substantial improvement in mean change in GAS ratings (35.0 and 33.8, respectively, for the valproate and valproate+lithium groups) and global evaluations, regardless of whether valproate was administered alone or in combination with lithium. As an anecdotal observation, certain patients did respond better to the combination of valproate and lithium, although this response did not happen frequently enough to reach statistical significance.

Over the past two decades, clinicians increasingly have used concomitant administration of a lithium drug and valproate, optionally with a third drug, to beneficially mitigate the mania and depression associated with BPD. For example, Sharma et al. reported treatment of rapid cycling BPD with combination therapy of valproate and lithium. [V. Sharma, E. Persad, D. Mazmanian, K. Karunaratne. Treatment of rapid cycling bipolar disorder with combination therapy of valproate and lithium. Can. J. Psychiatry 1993; 38: 137-139.]

In U.S. Patent Application 2005/0233010 Salow discloses combinatorial therapies for treating anxiety, depression or psychotic conditions using a co-therapy regimen comprising a lithium salt and a psychoactive drug selected from the group consisting of serotonin reuptake inhibitor, a $5HT_2$ receptor antagonist, an anticonvulsant, a norepinephrine reuptake inhibitor, an α-adrenoreceptor antagonist, an NK-3 antagonist, an NK-1 receptor antagonist, a PDE4 inhibitor, a neuropeptide Y5 Receptor Antagonist, a D4 receptor antagonist, a $5HT_{1A}$ receptor antagonist, a $5HT_{1D}$ receptor antagonist, a CRF antagonist, a monoamine oxidase inhibitor, a sedative-hypnotic drug, and an atypical psychotic. Exemplary forms of lithium salts include lithium carbonate, lithium citrate, lithium acetate, lithium glutamate, lithium orotate, lithium thionate, and lithium sulphate. Valproate is named as an anticonvulsant drug that may be co-administered with a lithium salt.

Lithium valproate has not, however, been available for clinical use. In the absence of lithium valproate, clinicians and patients have noted the following serious difficulties in treatment management. Concomitant administration of lithium with other antipsychotic drug(s) can unexpectedly increase intracellular lithium levels, a possible mechanism for unanticipated adverse interactions and resulting toxicity. Patients with bipolar disorder demonstrate poor compliance with dosing regimens that included two different drugs (i.e., a lithium drug and a valproate drug) and/or two different dosing regimens and suffer the occurrence of withdrawal mania. Poor compliance with the aforementioned dosing regimens also increases the risks of side effects and toxicity, including the possibility of permanent neurological sequelae with cerebellar damage. (Valproate toxicity includes dizziness; elevated SGPT, SGOT, alkaline phosphatases, and LDH values; and sedation and/or nausea. Lithium toxicity includes the potential for extrapyramidal side-effects, cogwheel rigidity, cerebellar tremor, incoordination, severe neurological symptoms, hyperthermia, impaired consciousness and irreversible brain damage.) [J. C. Cookson. The neuroendocrinology of mania. J Affect Disorders 1985; 8:233-241. M. Schou. Long-lasting neurological sequelae after lithium intoxication. Acta Psych. Scand. 1984; 70: 594-602.]

Among the drugs that have been studied as potential treatments for HAD are antioxidant medications, calcium channel antagonists, NMDA antagonists, platelet activating factor inhibitors, and drugs that inhibit glycogen synthase kinase 3 beta (GSK-3β) and mixed lineage kinase (MLK). Specifically, sodium valproate and lithium ion, existing epilepsy drugs, have proven to be GSK-3β inhibitors having strong potential as treatments for HAD. Schifitto et al., for example, conducted a pilot 10-week placebo-controlled study of valproate (250 mg twice daily) in 22 HIV-infected individuals with (n=16) and without (n=6) cognitive impairment. [G. Schifitto, D. R. Peterson, J. Zhong, H. Ni, K. Cruttenden, M. Gaugh, H. E. Gendelman, M. Boska, and H. Gelbard. Valproic acid adjunctive therapy for HIV-associated cognitive impairment. A first report. Neurology 2006.) Valproate was safe and well tolerated, with trends toward improved neuropsychological performance and brain metabolism in the impaired subjects.

In brief, clinicians have shown that both lithium (ion) and valproate are useful drugs for the treatment of neurological disorders. To date, however, the lack of availability of lithium valproate as a stable, non-hygroscopic valproate salt has prevented broader therapeutic applications of lithium valproate. The present invention remedies these shortcomings.

GENERAL DESCRIPTION OF THE INVENTION

Conventionally, combinations of lithium salts and valproate salts, administered independently, are used for the treatment of bipolar disorder and other neurological disorders, and are being evaluated as combination therapies for the treatment of immunological disorders and viral-related disorders. The present invention provides a heretofore unknown valproate salt, lithium valproate, together with methods for its preparation, formulation into pharmaceutical dosage forms, and therapeutic uses.

DETAILED DESCRIPTION OF THE INVENTION

Figure 1:
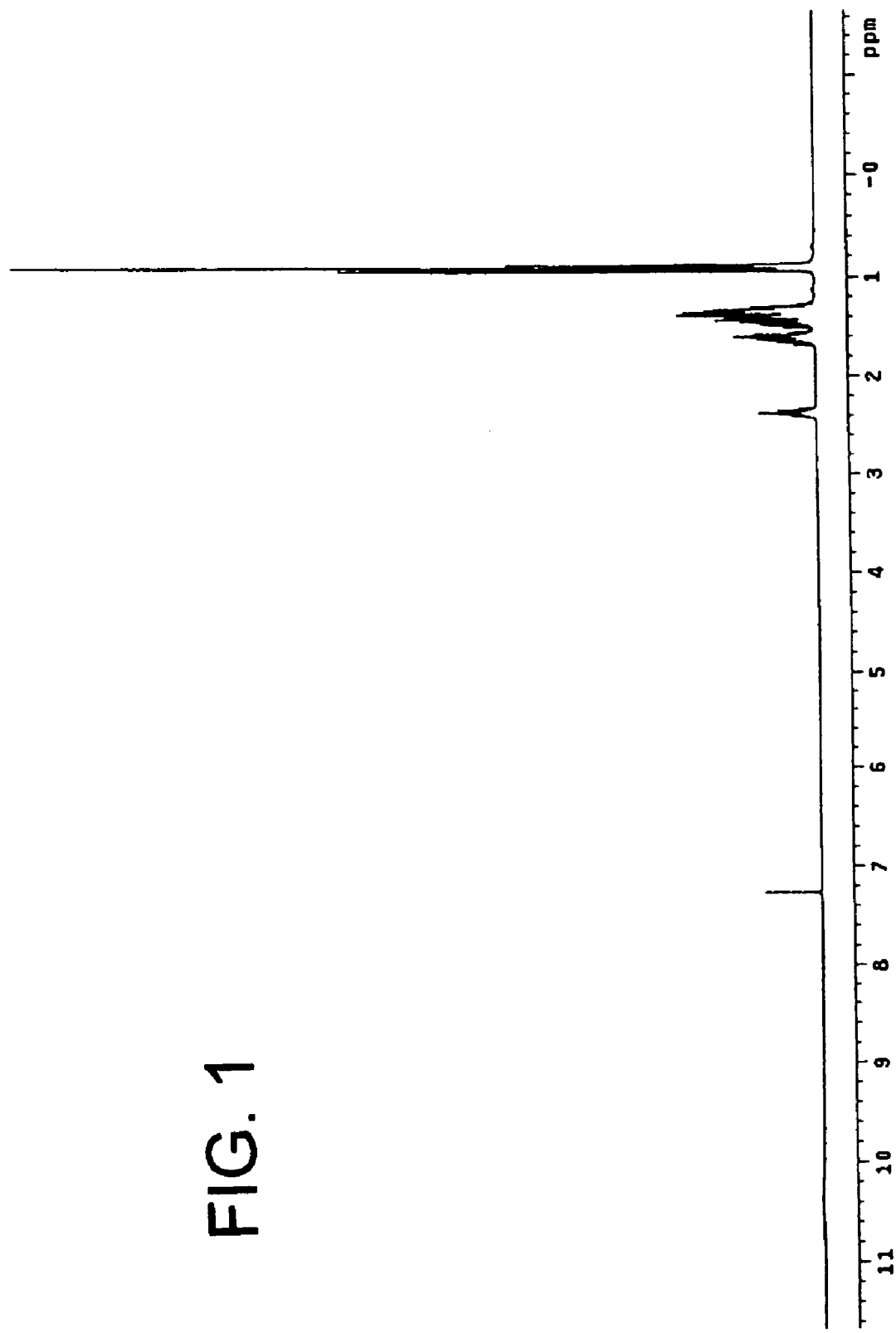
FIG. 1 is the $^1$H-Nuclear Magnetic Resonance ($^1$H-NMR) spectrum of valproic acid in perdeutero-methanol solution.

The present invention provides lithium valproate, a heretofore unknown valproate salt. A CAS Registry Number has not yet been assigned to this substance. The molecular formula of lithium valproate is $C_8H_{15}O_2Li$. By weight, its composition is 59.4% carbon, 9.8% hydrogen, 7.5% lithium, and 23.3% oxygen. Lithium valproate is about 4.6% lithium and 95.4% valproate by weight. Also within the scope of this invention are lithium valproate compositions having specific bulk densities or tap densities, and lithium valproate compositions having specific particle sizes. Further included within the scope of this invention are lithium valproate compositions coated with pharmaceutically acceptable materials intended to modify the release and/or bioavailability of the lithium valproate (e.g., Eudragit, microcrystalline cellulose, hydroxypropylmethylcellulose phthalate, and so forth).

The present invention relates to methods for preparing lithium valproate as a stable, non-hygroscopic solid that is suitable for pharmaceutical formulation and therapeutic use. Lithium valproate is a bioavailable source of both lithium ion and valproate, each of which is a drug that is useful for several clinical indications, including neurological disorders, including mania, manic episodes associated with bipolar disorder, epilepsy, and affective and attention deficit disorders. In addition, valproate is used for the prophylactic treatment, modulation and management of migraine headache, chronic pain, and neuropathic pain. Further, lithium is used for the treatment of bipolar disorder, both for treatment of acute mania and for prophylaxis against recurrence. Other psychiatric conditions that may be benefited by administration of lithium include recurrent severe depressions without manic episodes, schizoaffective psychosis, episodic alcoholism, periodic antisocial behavior, and periodic schizophrenic illness. Combinations of lithium salts and valproate salts, administered independently, are used for the treatment of bipolar disorder and other neurological disorders, and are being evaluated as combination therapies for the treatment of immunological disorders and viral-related disorders.

The present invention also relates to a method of formulating lithium valproate in solid dosage forms or in water or aqueous solutions in concentrations that provide a therapeutically effective amount of lithium and/or valproate to a warm-blooded animal after the formulation is administered to the animal.

According to the methods of the present invention, lithium valproate is administered, alone or in combination with other therapeutically active or inactive substances, as a therapeutically effective and biologically available (i.e., bioavailable) source of lithium (ion) and valproate that are useful for the treatment of neurological, immunological, and viral-related disorders. Therapeutically effective concentrations of lithium valproate are a useful treatment and prophylaxis against recurrence for neurological disorders, including mania, manic episodes associated with bipolar disorder, epilepsy, and affective and attention deficit disorders; for the prophylactic treatment, modulation and management of migraine headache, chronic pain, and neuropathic pain; for the treatment of bipolar disorder, both for treatment of acute mania and for prophylaxis against recurrence; for the treatment of recurrent severe depressions without manic episodes, schizoaffective psychosis, episodic alcoholism, periodic antisocial behavior, and periodic schizophrenic illness; and for the treatment of immunological disorders and viral-related disorders, including HIV-related dementia.

The term "alkoxide of a lower alcohol" as used herein means the oxy anion of an alcohol having from 1 to 6 carbons, arranged linearly or branched. Preferred alkoxides of the present invention are methoxide, ethoxide, propoxide, isopropoxide, butoxide, and t-butoxide.

The term "excipient material" means any compound forming a part of the formulation, which is not intended to have independent biological activity, and which is added to a formulation to provide specific characteristics to the dosage form, including providing protection to the active ingredient from chemical degradation (for example, a polymer coating such as hydroxypropyl methylcellulose or Eudragit, or an anti-oxidant such as L-cysteine HCl or sodium metabisulfite), facilitating release of a tablet or caplet from the contact surfaces of manufacturing equipment (for example, magnesium stearate), and so forth.

By the terms "treating" and "treatment" and the like are used herein to generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein encompasses any treatment of a disease in a mammal, particularly a human and includes: (a) preventing the disease from occurring in a subject which may be predisposed to the disease but has not yet been diagnosed as having it; (b) inhibiting the disease or arresting its development; (c) relieving the disease, causing regression of the disease and/or its symptoms or conditions; or (d) returning a clinical value to the concentration range normally found in a subject.

The phrase "therapeutically effective" is intended to qualify the amount of lithium valproate for use in the orally or intravenously administered therapy which will achieve the goal of providing a biologically available (i.e., bioavailable) concentration of the drugs lithium and valproate to effect reducing or preventing, for example, a neurological, immunological, or viral-related disorder, while avoiding adverse side effects typically associated with valproic acid, sodium valproate compositions, or other valproate salts.

Included within the scope of this invention is a method of treating neurological disorders, immune disorders, or viral-related disorders in a warm-blooded animal using pharmaceutical compositions comprising lithium valproate and a suitable pharmaceutical carrier. Also included within the scope of this invention is a method of treating neurological disorders, immune disorders, or viral-related disorders in a warm-blooded animal using pharmaceutical compositions comprising lithium valproate and a suitable pharmaceutical carrier, or pharmaceutical compositions comprising lithium valproate, a linear or branched alcohol having from 1 to about 6 carbon atoms, or an organic polyol having from 2 to 100 hydroxyl groups, and a suitable pharmaceutical carrier.

For the purpose of this disclosure, a warm-blooded animal is a member of the animal kingdom which includes but is not limited to mammals and birds. The most preferred mammal of this invention is human.

Surprisingly, the inventors have discovered methods for the preparation of a heretofore unknown valproate salt, lithium valproate, which afford significant advantages, particularly in pharmaceutical manufacturing and formulation. Thus, lithium valproate of the present invention, a white solid, is recovered in high yields from reactions of valproic acid and a lithium alkoxide in solutions of a lower alcohol and a hydrocarbon solvent.

Even more surprisingly, the inventors have discovered that lithium valproate is recovered in high yields from reactions of valproic acid and a lithium alkoxide in a hydrocarbon solvent. Preferably, the lithium alkoxide is lithium t-butoxide and the hydrocarbon solvent is hexane.

The lithium valproate solid thus obtained has high purity, is free of contaminating inorganic and organic lithium salts and residual solvents, is not hygroscopic or deliquescent, and is stable during storage. Further, the lithium valproate of the present invention readily dissolves in water or aqueous solutions to provide aqueous solutions having a lithium concentration in the range from about 0.04 mg/mL to about 10 mg/mL and a valproate concentration in the range from about 1 mg/mL to about 250 mg/mL and near neutral pH.

Lithium valproate of the present invention is a white solid having the molecular formula $C_8H_{15}O_2Li$. By weight, its composition is 63.99% carbon, 10.07% hydrogen, 4.62% lithium, and 21.32% oxygen. Lithium valproate is about 4.6% lithium and 95.4% valproate by weight.

A conventional method for the preparation of an alkali metal salt of an organic acid is by reacting a metal oxide, metal bicarbonate, metal carbonate, or metal hydroxide with a carboxylic acid in a lower alcohol solution, as disclosed, by way of example, by Trusovs in U.S. Pat. No. 6,670,494. Attempts to prepare lithium valproate by this conventional approach failed to provide lithium valproate solid of the present invention. Reaction of lithium hydroxide with valproic acid in ethanol, for example, provided an intractable, brown oil that failed to crystallize. When lithium carbonate was substituted for lithium hydroxide in the reaction, the ethanol solution never became clear, and it was difficult to monitor the progress of the reaction and isolate the desired product, lithium valproate, from residual lithium carbonate salts.

After extensive experimentation, we discovered that reaction of valproic acid with a lithium alkoxide in alcohol solution provided, after addition of a low-boiling hydrocarbon (such as petroleum ether, pentane, hexane, heptane, octane, benzene, toluene, or xylene, for example), lithium valproate as a white solid that was stable and non-hygroscopic. Further, we discovered to our surprise that the reaction could be simplified by carrying out the synthesis in a low-boiling hydrocarbon by reacting valproic acid and a molar equivalent of lithium alkoxide in the hydrocarbon. Under these conditions, lithium valproate precipitated and was isolated by filtration. Conveniently, a solution of lithium t-butoxide in hexane is commercially available, but solutions of other lithium alkoxides in other hydrocarbons are also useful in this method of preparation and are prepared by reaction of lithium metal with an alcohol in a hydrocarbon solvent.

The methods for the preparation of lithium valproate that are disclosed herein are advantageously useful in pharmaceutical manufacturing of this valproate salt, as illustrated by way of example, by the following. The raw materials and solvents are commercially available. The reaction conditions enable control of reaction temperature, monitoring of the progress of reaction for extent of completion, methods for the removal of impurities, and convenient and high yield steps for the recovery of lithium valproate from the solution.

The lithium valproate obtained by the methods of the present invention exhibits both high purity and absence of both solvents and chemical and biological contaminants, qualities qualifying it for use in pharmaceutical formulations. The lithium valproate of the present invention is a white solid that is not hygroscopic or deliquescent and is stable during storage. Further, this valproate salt is easily milled or processed into formulary dosage forms using conventional methods and techniques.

In general, the solubilities of lithium salts of organic acids in water or aqueous solutions vary unpredictably. Lithium carbonate, for example, is slightly soluble in water and insoluble in ethyl alcohol. Lithium acetate is soluble in water and ethyl alcohol. Lithium citrate is soluble in water and slightly soluble in ethyl alcohol. Surprisingly, the inventors have found that formulations of lithium valproate in aqueous solution are readily prepared by dissolving lithium valproate of the present invention in water or aqueous solutions containing ethyl alcohol or a polyol, such as propylene glycol, polyethylene glycol, mannitol, xylitol, or dextrose. In this manner, clear and colorless aqueous solutions of lithium valproate are reproducibly obtained, wherein the concentrations of lithium and valproate in solution are in the range from about 0.04 mg/mL to 10 mg/mL lithium and from about 1 mg/mL to about 250 mg/mL valproate, respectively.

The availability of lithium valproate of the present invention as a pharmaceutical quality compound of known composition and exhibiting thermal stability and an absence of hygroscopicity is particularly important for pharmaceutical and therapeutic applications of lithium valproate. Lithium valproate as provided herein may be formulated to provide known concentrations of lithium and valproate. In this manner, dosage forms having known quantities of lithium valproate can be prepared for administration to a subject by any of a variety of routes, including oral, parenteral, and inhalation. The inventors expect that the concomitant provision of lithium and valproate as lithium valproate of the present invention will be particularly useful in the treatment of children or small adults having neurological or viral disorders.

Lithium valproate of the present invention affords significant advantages in treatment management to both clinicians and patients. Since lithium valproate of the present invention provides both lithium ion and valproate in known concentrations, a requirement for the separate but concomitant administration of both a lithium drug and a valproate drug is eliminated. Patients with bipolar disorder demonstrated poor compliance with dosing regimens that included two different drugs (i.e., a lithium drug and a valproate drug) and suffered the occurrence of withdrawal mania. Poor compliance with the aforementioned dosing regimens also increased the risks of side effects and toxicity, including the possibility of permanent neurological sequelae with cerebellar damage. Concomitant administration of conventional lithium salts with other antipsychotic drug(s) can unexpectedly increase intracellular lithium levels, a possible mechanism for unanticipated adverse interactions and resulting toxicity. Lithium valproate of the present invention provides known quantities of lithium and valproate and is expected to prevent these unexpected increases.

Dosage Forms. The pharmaceutical compositions of this invention can be administered by any means that effects contact of the active ingredients with the site of action in the body of a warm-blooded animal. For example, the means can be oral, transdermal, by inhalation, or parenteral (i.e., subcutaneous, intravenous, intramuscular or intraperitoneal). Alternatively or concurrently, the means of administration can be by more than one route (e.g., oral and parenteral). A most preferred means of administration is by the oral route (i.e., ingestion).

The active ingredients can be administered by the oral route in solid dosage forms, such as tablets, capsules, and powders, or in liquid dosage forms, such as elixirs, syrups, and suspensions. The pharmaceutical compositions of this invention also can be administered parenterally, in sterile liquid dosage forms. The pharmaceutical composition is preferably made in the form of a dosage unit containing a particular amount of each active ingredient.

In general, the pharmaceutical compositions of this invention can be prepared by conventional techniques, as are described in Remington's Pharmaceutical Sciences, a standard reference in this field [Gennaro A R, Ed. Remington: The Science and Practice of Pharmacy. 20$^{th}$ Edition. Baltimore: Lippincott, Williams & Williams, 2000]. For therapeutic purposes, the active components of this combination therapy invention are ordinarily combined with one or more adjuvants appropriate to the indicated route of administration. If administered per os, the components may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tabletted or encapsulated for convenient administration. Such capsules or tablets may contain a controlled-release formulation as may be provided in a dispersion of active compound in hydroxypropyl methylcellulose. Solid dosage forms can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Both the solid and liquid oral dosage forms can contain coloring and flavoring to increase patient acceptance.

Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The components may be dissolved in water, polyethylene glycol, propylene glycol, ethanol, corn oil, cottonseed oil, peanut oil, sesame oil, benzyl alcohol, sodium chloride, and/or various buffers. The indicated formulations can contain compatible auxiliaries and excipients, such as anti-oxidants, preservatives, stabilizing agents, emulsifiers, salts for influencing the osmotic pressure, and/or buffer substances.

Other adjuvants and modes of administration are well and widely known in the pharmaceutical art.

Pharmaceutical compositions for use in the treatment methods of the invention may be administered in oral form or by intravenous administration. Oral administration of the therapy is preferred. Dosing for oral administration may be with a regimen calling for single daily dose, or for a single dose every other day, or for multiple, spaced doses throughout the day. The active agents which make up the therapy may be administered simultaneously, either in a combined dosage form or in separate dosage forms intended for substantially simultaneous oral administration. The active agents which make up the therapy may also be administered sequentially, with either active component being administered by a regimen calling for two-step ingestion. Thus, a regimen may call for sequential administration of the active agents with spaced-apart ingestion of the separate, active agents. The time period between the multiple ingestion steps may range from a few minutes to several hours, depending upon the properties of each active agent such a potency, solubility, bioavailability, plasma half-life and kinetic profile of the agent, as well as depending upon the age and condition of the patient. The active agents of the therapy whether administered simultaneously, substantially simultaneously, or sequentially, may involve a regimen calling for administration of one active agent by oral route and the other active agent by intravenous route. Whether the active agents of the therapy are administered by oral or intravenous route, separately or together, each such active agent will be contained in a suitable pharmaceutical formulation of pharmaceutically-acceptable excipients, diluents or other formulations components.

Clinical Uses of Lithium Valproate

The present invention provides methods for the reproducible preparation of pharmaceutical quality lithium valproate as well as methods for its formulation into pharmaceutical dosage forms using conventional pharmaceutical techniques. In addition, the inventors have shown that aqueous solutions of lithium valproate are readily prepared to have lithium concentrations in the range from about 0.4 mg/mL to about 12.5 mg/mL and and valproate concentrations from about 1 mg/mL to about 250 mg/mL. Aqueous solutions of lithium valproate comprise fully ionized solutions of lithium ions and valproate ions which, after parenteral administration to a subject, are completely bioavailable. The inventors have also shown that lithium valproate is soluble in simulated gastric fluid USP and in simulated intestinal fluid USP. Given this solubility, the inventors expect that lithium valproate, when administered per os to a subject, will exhibit a bioavailability at least about 90% relative to intravenous infusion, a bioavailability that is equivalent to or exceeds that of divalproex sodium. On these bases, therefore, the inventors expect that lithium valproate of the present invention will be administered to subjects in need of valproate therapy as a therapeutically effective and biologically available substitute for valproic acid, divalproex sodium, valproate sodium, and other valproate salt compositions.

For example, the inventors expect that lithium valproate of the present invention will be substituted for valproic acid, divalproex sodium, valproate sodium and other valproate salt compositions in compositions useful for the treatment of neurological disorders as disclosed, by way of example, in U.S. Patent Applications 20050095579, 20050090548, 20050090449, 20050075282, 20050070524, and 20050065340, as well as in U.S. Pat. Nos. 6,406,716, 6,323,236, 6,287,598, and 5,945,416 and in international patents EP 1371366 A1, EP 0966967 A3, EP 1158973 B1, WO 2005070461, WO 2005063297, WO 2005051915, WO 2005049040, and WO 2004101603. Further, the inventors expect that lithium valproate of the present invention will be substituted for valproic acid, divalproex sodium, valproate sodium and other valproate salt compositions in compositions useful for the treatment of immunological disorders as disclosed, by way of example, in U.S. Patent Applications 20050119261, 20050090553, 20050065596, 20050065173, 20050054091, as well as in U.S. Pat. Nos. 5,506,224 and 5,432,176 and in international patents EP 1529527 A1, EP 1293205 A1, EP 1170008 A1, EP 1301184 B1, WO 2005023179, WO 2005018578, WO 2004113305, WO 2004096216, WO 2004096224, and WO 2004050076. Likewise, the inventors expect that lithium valproate of the present invention will be substituted for valproic acid, divalproex sodium, valproate sodium and other valproate salt compositions in compositions useful for the treatment of viral-related disorders as disclosed, by way of example, in the report of Smith [Retrovirology Sep. 19, 2005, 2(1): 56], Cohen [Science Aug. 12, 2005, 309(5737): 999-1000], Lehrman et al. [Lancet Aug. 13, 2005, 366(9485): 549-555], and Ylisastigui et al. [AIDS May 21, 2004, 18(8): 1101-1108].

The inventors expect that lithium valproate of the present invention will have particular therapeutically beneficial when administered to a warm-blood mammal for the treatment of neurological disorders, including bipolar disorders and HIV-associated dementia.

The inventors further expect that the pharmacokinetics of particularly favorable embodiments of lithium valproate of the present invention allow for administration of total daily doses of lithium as small as 25 mg/day, 30 mg/day, 40 mg/day, or 50 mg/day, or lower. In other words, lithium valproate of the present invention will, we expect, be useful for administration of doses of lithium and valproate which may be of particular benefit for children or individuals of small stature and weight.

The following examples present representative compositions of the present invention. The examples are representative of the scope of the invention, and as such are not to be considered or construed as limiting the invention recited in the appended claims.

Example 1

Attempted preparation of lithium valproate. A conventional method for the preparation of salts of organic acids is by reaction of a metal hydroxide or carbonate with an organic acid. Valproic acid (2 g, 0.0138 mol) was dissolved in 40 mL of ethanol, and a slurry of lithium hydroxide (0.56 g, 0.0138 mol) in 10 mL of ethanol was added. The resulting reaction mixture was stirred at room temperature for 3 hours. The color of the solution changed from colorless to brown during this time. Stirring was continued for an additional hour, and then the reaction mixture was filtered to remove residual solids (0.17 g). The filtrate was concentrated under vacuum to a residual oil. Even after trituration with organic solvents, the oil did not crystallize or provide a solid of known composition. The reaction failed to provide lithium valproate solid.

Example 2

Figure 2:
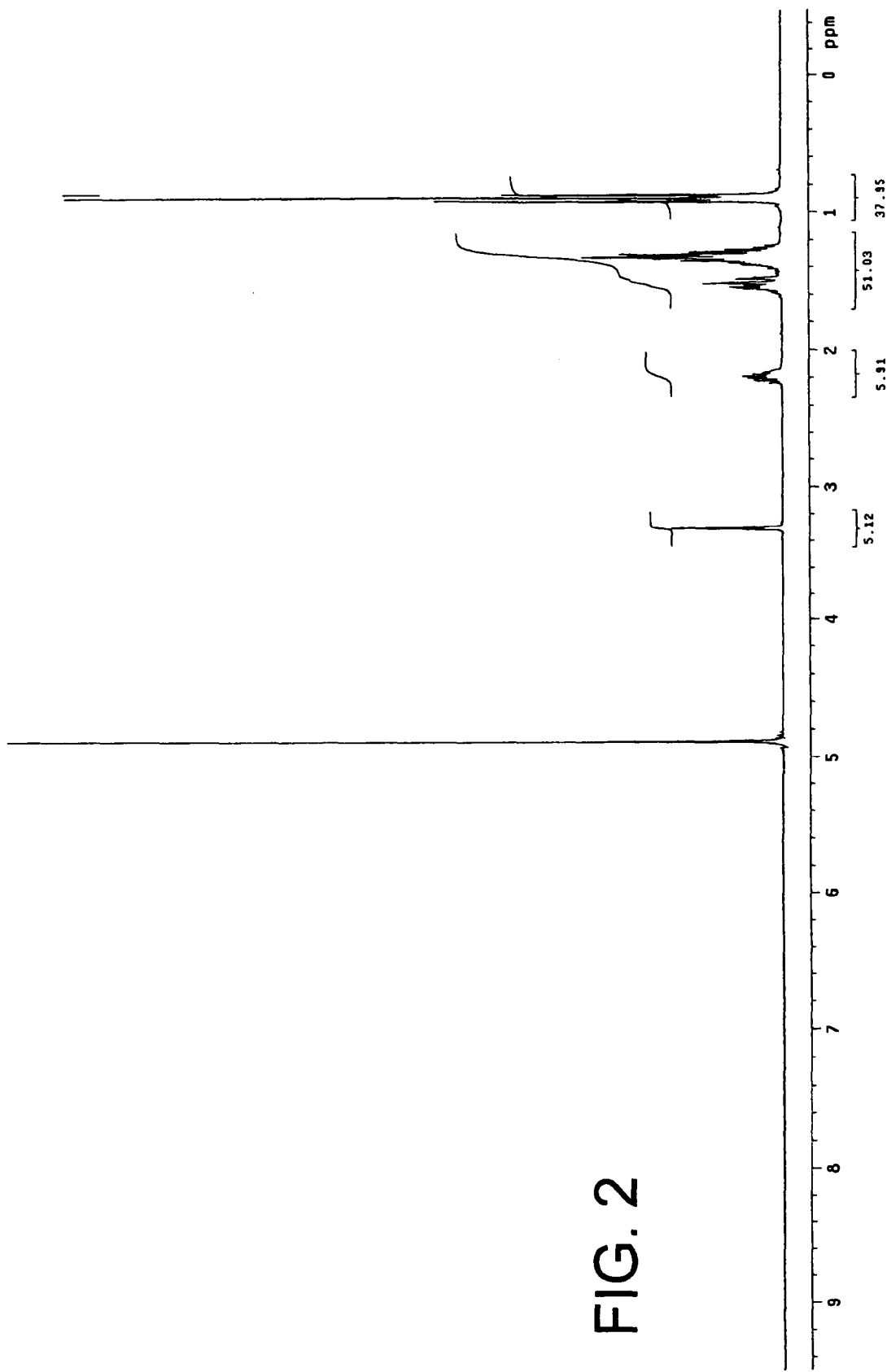
FIG. 2 is the $^1$H-NMR spectrum of lithium valproate in perdeutero-methanol solution.

Preparation of lithium valproate of the present invention. Valproic acid (2.7 g, 0.018 mol) was dissolved in 25 mL of ethanol to provide a clear, colorless solution. One equivalent of lithium t-butoxide (as a 1 M solution in hexane) was added dropwise. At the completion of the addition, a white solid formed, and 15 mL of hexane was added to facilitate stirring. Stirring was continued for an hour, and 25 mL of hexane was added. The solid was isolated by filtration and dried to constant mass (1.7 g, 63% of theoretical). Additional product (0.4 g, 14% of theoretical) was obtained by concentration of the filtrate under vacuum and cooling. The product, lithium valproate, was a white solid that did not melt at a temperature less than 300° C. (the highest temperature tested). The product was very soluble in water and methanol. The $^1$H-NMR spectrum of a perdeutero-methanol solution of the product (FIG. 2) differed from that of valproic acid (FIG. 1) and confirmed that the product was a valproate salt. (Lithium is not detected by $^1$H-NMR.)

Example 3

Preparation of lithium valproate of the present invention. Valproic acid (2.7 g, 0.018 mol) was dissolved in 25 mL of hexane to provide a clear, colorless solution. One equivalent of lithium t-butoxide (as a 1 M solution in hexane) was added dropwise. At the completion of the addition, a white solid formed. Stirring was continued for an hour. The solid was isolated by filtration and dried to constant mass (2.4 g, 85% of theoretical). Additional product (0.4 g, 14% of theoretical) was obtained by concentration of the filtrate under vacuum and cooling. The product, lithium valproate, was a white solid that did not melt at a temperature less than 300° C. (the highest temperature tested). The product was very soluble in water and methanol. The $^1$H-NMR spectrum of lithium valproate (FIG. 2) differed from that of valproic acid (FIG. 1) and confirmed that the product was a valproate salt. (Lithium is not detected by $^1$H-NMR.)

Example 4

Valproate analysis by HPLC. Weight percent valproate was determined by reversed-phase HPLC analysis using the following conditions:

Column: X-Terra Reversed-Phase C18, 5 μM particle size, 4.6 mm i.d.×250 cm length (Waters)

Mobile Phase A: Acetonitrile (ACN):Water:Trifluoroacetic acid (TFA) 10:90:0.1 (v/v/v)

Mobile Phase B: ACN:TFA 100:0.1 (v/v)

Separation Conditions: Isocratic delivery of A and B in a 60:40 volume ratio of A:B Flow Rate: 1.0 mL/min Detection Wavelength: 210 nm Sample Diluent: Water containing 0.1% TFA Injection Volume: 5.0 μL Valproate Retention Time: 9.3 minutes Acquisition Time: 12 minutes Valproate standards with concentrations ranging from 0.05 μg/mL to 0.5 μg/mL were prepared by dissolution of aliquots of valproic acid and analyzed in triplicate to provide a standard curve, which exhibited a linearity, R, of 0.99998. Peak tailing of the valproate response was less than 2.0. Test samples were prepared by accurately weighing approximately 40 mg of sample, quantitatively transferring the solid to a 100-mL volumetric flask and diluting with water containing 0.1% TFA. Sample analyses were completed in triplicate. Relative standard error of analysis was 1% or less. Sample analyses confirmed the presence of valproate.

Example 5

Preparation of Aqueous Solutions of Lithium Valproate. Aqueous solutions of lithium valproate were prepared in the following manner. Portions of lithium valproate of the present invention were added to 1 mL of water and stirred to effect dissolution. Addition continued until an added portion of lithium valproate failed to dissolve. The solubility of lithium valproate was determined as about 250 mg of lithium valproate per mL of water.

Example 6

Lithium and valproate, independently administered, in the treatment of primary psychiatric disorders. The study summarized below was reported by Stephen G. Hayes, M.D., in Journal of Clinical Psychiatry 50 (3, Suppl), pages 35-39. Thirty-five patients, all with major depressive illness, bipolar disorder, or schizoaffective disorder, were retrospectively identified as having received valproate either alone or in combination with lithium, after having failed to respond adequately to previous lithium and/or carbamazepine treatment. Clinical evaluation and Global Assessment Scale (GAS) scores indicated that at baseline all but 3 of the patients experienced serious psychiatric symptoms, serious impairment in social or professional functioning, or significant impairment in reality testing. Mean GAS scores after a mean duration of at least 1 year of valproate administration improved in 7 of 9 depressed patients, 12 of 12 patients with bipolar disorder, and 11 of 14 patients with schizoaffective states. For patients with either depressive disorders or mixed bipolar disorders, that mean change represented a level of improvement sufficient to elevate the majority of the patients into the mild symptom range or the virtually asymptomatic state. The responses of patients with bipolar and schizoaffective disorders to valproate treatment compared to valproate plus lithium treatment were also evaluated. Patients in both diagnostic categories demonstrated very similar and quite substantial improvement in mean change in GAS ratings and global evaluations, regardless of whether valproate was administered alone or in combination with lithium.

The following example presents a hypothetically useful therapeutic use of representative pharmaceutical compositions of the present invention and the anticipated outcomes in treating neurological diseases in subjects requiring such treatment. The example is representative of the scope of the invention, and as such is not to be considered or construed as limiting the invention recited in the appended claims.

Example 7

Lithium valproate of the present invention in the treatment of primary psychiatric disorders. A study is completed that is similar to the one reported by Stephen G. Hayes, M.D., in Journal of Clinical Psychiatry 50 (3, Suppl), pages 35-39. Thirty-five patients, all with major depressive illness, bipolar disorder, or schizoaffective disorder, will be identified as having received valproate either alone or in combination with lithium, after having failed to respond adequately to previous lithium and/or carbamazepine treatment. Clinical evaluation and Global Assessment Scale (GAS) scores will be completed and will indicate that at baseline more than 90% of the patients experience serious psychiatric symptoms, serious impairment in social or professional functioning, or significant impairment in reality testing. After a mean duration of at least 1 year of lithium valproate administration, the following results are expected. Mean GAS scores improve in at least about 60% of depressed patients, at least about 90% of patients with bipolar disorder, and at least about 75% of patients with schizoaffective states. For patients with either depressive disorders or mixed bipolar disorders, that mean change is expected to represent a level of improvement sufficient to elevate the majority of the patients into the mild symptom range or the virtually asymptomatic state.

All mentioned references are incorporated by reference as if here written. When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

Without further elaboration, it is believed that one skilled in the art can, using the preceding description, utilize the present invention to its fullest extent. The specific embodiments are, therefore, to be construed as merely illustrative, and not limitative of the remainder of the disclosure in any way whatsoever.

We claim:

1. A solid composition comprising lithium valproate of high purity consisting essentially of a non-hygroscopic white solid having the molecular formula $C_8H_{15}O_2Li$, a weight percent lithium and valproate content of about 4.6% and 95.4% respectively, not melting at temperatures less than 300 degrees C., made by the method of adding a lithium alkoxide to valproic acid in a hydrocarbon solution, and recovering the solid lithium valproate therefrom by filtration, wherein said composition is characterized in being substantially free of contaminating inorganic and organic lithium salts and residual solvents.

2. A method of formulating lithium valproate in a solid dosage form comprising admixing a therapeutically effective amount of the lithium valproate of claim 1 with an adjuvant and compressing into a tablet or encapsulated tablet.

3. A formulation of lithium valproate in solid dosage form comprising a therapeutically effective amount of the lithium valproate of claim 1 admixed with an adjuvant.

4. The adjuvant of claims 2 and 3 wherein said adjuvant is selected from the group consisting of lactose, sucrose, starch powder, cellulose esters of alkanoic acids, cellulose alkyl esters, talc, stearic acid, magnesium stearate, magnesium oxide, sodium and potassium salts of phosphoric and sulfuric acids, gelatin, acacia gum, sodium arginate, polyvinylpyrrolidone, and polyvinyl alcohol, or combinations thereof.

* * * * *